US006100098A

United States Patent [19]

Newkirk

[11] Patent Number: 6,100,098

[45] Date of Patent: Aug. 8, 2000

[54] ANTI-AGE IGG AND USES THEREOF FOR THE DIAGNOSIS OF SEVERE DISEASE

[75] Inventor: Marianna M. Newkirk, Pierrefonds, Canada

[73] Assignee: McGill University, Montreal, Canada

[21] Appl. No.: 09/024,053

[22] Filed: Feb. 17, 1998

Related U.S. Application Data

[60] Provisional application No. 60/038,406, Feb. 18, 1997.

[51] Int. Cl.[7] .................... G01N 33/564

[52] U.S. Cl. .................... 436/507; 436/509; 435/7.1; 435/7.92; 530/387.2; 530/868

[58] Field of Search .................... 436/507, 509; 435/7.1, 7.92; 530/387.2, 868

[56] References Cited

PUBLICATIONS

Dolhofer–Bliesener et al., *Scand. J. Clin. Lab. Invest.,* 50:739–746, 1990.
Hennessey et al., *J. Parent. & Enter. Nutrit.,* 15.60–64, 1991.
Sasaki et al., *Clin. Chim. Acta,* 220.119–121, 1993.
Corper et al., *Nature Struct. Biol.,* 4:374–381, 1997.
Pokharna et al., *J. Ortho, Res.,* 13:13–21, 1995.
Mashiba et al., *Clin. Chim. Acta,* 212:3–15, 1992.
Mizutari et al., *J. Invest. Dermatol.* 108:797–802, 1997.
Takahashi et al., *Br. J. Rheum.* 36:637–642, 1997.
Newkirk et al., *Arthritis Rheum.* 40(suppl. 1):S247, 1997.
Kemper et al., *Ann. Intern. Med.* 46:831–851, 1957.
Yan et al., *Nature,* 382:685, 1996.
Breitner et al., *Neurology,* 44:227, 1994.
Myllykangas–Luosujarvi et al., *Br. J. Rheumatol.,* 33(5):501–502, 1994.

*Primary Examiner*—Christina Y. Chan
*Assistant Examiner*—Patrick J. Nolan
*Attorney, Agent, or Firm*—David S. Resnick; Nixon Peabody LLP

[57] ABSTRACT

The present invention relates to the diagnosis of severe diseases based on the determination of the presence of AGE-IgG autoantibodies in patients and to a method of treatment thereof. More precisely, the invention relates to a method for the diagnosis of severe diseases in patients, which comprises the steps of: a) incubating a solid support coated with an AGE antibody with a biological sample from said patient for a time sufficient for an immunoreaction to occur; and b) determining the presence of AGE-IgG autoantibodies present in said sample; whereby the presence of AGE-IgG autoantibodies in said patient's sample is indicative of a severe disease. Such severe diseases which may be diagnosed in accordance with the present invention include Rheumatoid arthritis, atherosclerosis, amyloidosis, diabetes, Henoch Schonlein Purpura, Crohn's disease and Coeliac disease.

2 Claims, 3 Drawing Sheets

Lane 1 and 2, human IgG2, lane 2 AGE modified *in vitro*; lane 3-7 2.5% PEG precipitate from patients with RA (lanes 5-7, same patient at different time points); lanes 8,9 2.5% PEG precipitates from normal controls; Lanes 10, 2.5% PEG precipitate from I.D.D.M HbA1c=9.5; Lane 11 2.5% PEG precipitate from Type II diabetic HbA1c=11.7; Lane 12 purified normal polyclonal IgG; HC, heavy chain; LC, light chain.

ANTI-AGE IGG AND USES THEREOF FOR THE DIAGNOSIS OF SEVERE DISEASE

This application claims benefit of Provisional Application Ser. No. 60/038,406 filed Feb. 18, 1997.

BACKGROUND OF THE INVENTION (a) Field of the Invention

The invention relates to the diagnosis of severe diseases based on the determination of the presence of AGE-IgG autoantibodies in patients.

(b) Description of Prior Art

Rheumatoid arthritis (RA) and diabetes (both type I and type II) are chronic diseases which are very costly to society, both in terms of reduced productivity and quality of life of the afflicted individuals, and in terms of the increased health care costs. The exact causes of RA and diabetes are unknown at present but appear to be multifactorial with both genetics (polygenic) and environmental factors playing important roles. We have recently discovered a new autoantigen/autoantibody system in RA which may provide insight into the pathogenesis and lead to new more effective therapies.

In patients with elevated blood glucose levels and/or oxidative stress, a large number of proteins can be non-enzymatically glycated, whereby the glucose molecules bind to the exposed amino acids lysine and arginine. Not all lysines and arginines are glycated on proteins of individuals with high blood glucose and/or oxidative stress. There are three key factors that influence the number and extent of protein glycation, namely the blood glucose level, the half-life of the protein in question (long lived proteins are more heavily glycated) and the number of lysines and arginines in the correct microenvironment in the protein. These are likely the surface exposed lysines, or as in the case of hemaglobin the amino terminal valine, which is adjacent to another basic amino acid (lysine or histadine). For example, in albumin, only 10 of 59 lysines are glycated. With time the sugar is bound irreversibly. Proteins with this modification are said to have advanced glycation end products (AGE). A well studied protein, hemoglobin-AGE (HbAlC) is used to monitor type 1 diabetics for insulin compliance. To date AGE-modified proteins have been suggested to have a role in atherosclerosis, amyloidosis and the complications of diabetes.

Antibody molecules, of all subclasses have lysine and arginine residues on their external surfaces which can be modified by advanced glycation end-products. Previous studies have shown that both IgG and IgM can be glycated (Dolhofer-Bliesener, et al., Scand. J. Clin. Lab. Invest. 50:739–746, 1990; Hennessey, et al. J. Parent. & Enter. Nutrit. 15, 60–64, 1991). The half-lives of the classes and subclasses of immunoglobulin in circulation vary, with IgGl, 2 and 4 having the longest half lives of 23 days. Previous reports have determined that there is a loss of Fc receptor function, namely in the ability to bind complement and protein A when the AGE modifications are present. There is also a report of loss of antigen binding when a mouse monoclonal was AGE modified (Sasaki et al., Clin. Chim. Acta, 220:119–121, 1993).

Up to 70% of patients with RA have circulating antibodies, generally in high amounts, called rheumatoid factors (RF) which bind to the Fc part of IgG antibodies. The presence of these antibodies is used to help diagnose the disease. Although RFs can be of any subclass, IgM RFs are the best studied. Characterization of RF structure (genes, degree of somatic mutation), binding specificity and role in disease pathogenesis has been the subject of much research. The binding site for RF binding to the IgG is in the CH2 to CH3 cleft, and based on the recent crystallographic data of a monoclonal RF completed to IgG Fc (Corper et al.. Nature Struct. Biol. 4:374–381, 1997), it appears that lysine at 437 and arginine at 255 on the IgG are in, or adjacent to the mapped binding site.

It would be highly desirable to be able to determine whether RFs could bind to AGE modified IgG.

It would be highly desirable to be provided with a diagnostic tool for the diagnosis of severe diseases based on the determination of the presence of AGE-IgG autoantibodies in patients.

SUMMARY OF THE INVENTION

One aim of the present invention is to provide a diagnostic tool for the diagnosis of severe diseases based on the determination of the presence of AGE-IgG autoantibodies in patients.

In the course of our investigations we found that a subset of patients had autoantibodies to the AGE-modified IgG.

In accordance with the present invention there is provided a method for the diagnosis of severe diseases in patients, which comprises the steps of:

a) incubating a solid support coated with an AGE antibody with a biological sample from the patient for a time sufficient for an immunoreaction to occur;

b) determining the presence of AGE-IgG autoantibodies present in the sample; whereby the presence of AGE-IgG autoantibodies in the patient's sample is indicative of a severe disease.

Such severe diseases which may be diagnosed using the method of the present invention are selected from the group consisting of Rheumatoid arthritis, atherosclerosis, amyloidosis, diabetes, Henoch Schonlein Purpura, Crohn's disease and Coeliac disease.

In accordance with the present invention there is provided a method of treatment a severe disease in a patient wherein the presence of AGE-IgG autoantibodies in a biological sample of the patient was detected, which comprises administering a non-corticosteroids medicament to maintain patient's blood glucose at a normal or low level to prevent non-enzymatic glycation.

The severe diseases which may be treated in accordance with this method are selected from the group consisting of Rheumatoid arthritis, atherosclerosis, amyloidosis, diabetes, Henoch Schonlein Purpura, Crohn's disease and Coeliac disease.

DETAILED DESCRIPTION OF THE INVENTION

Figure 1:
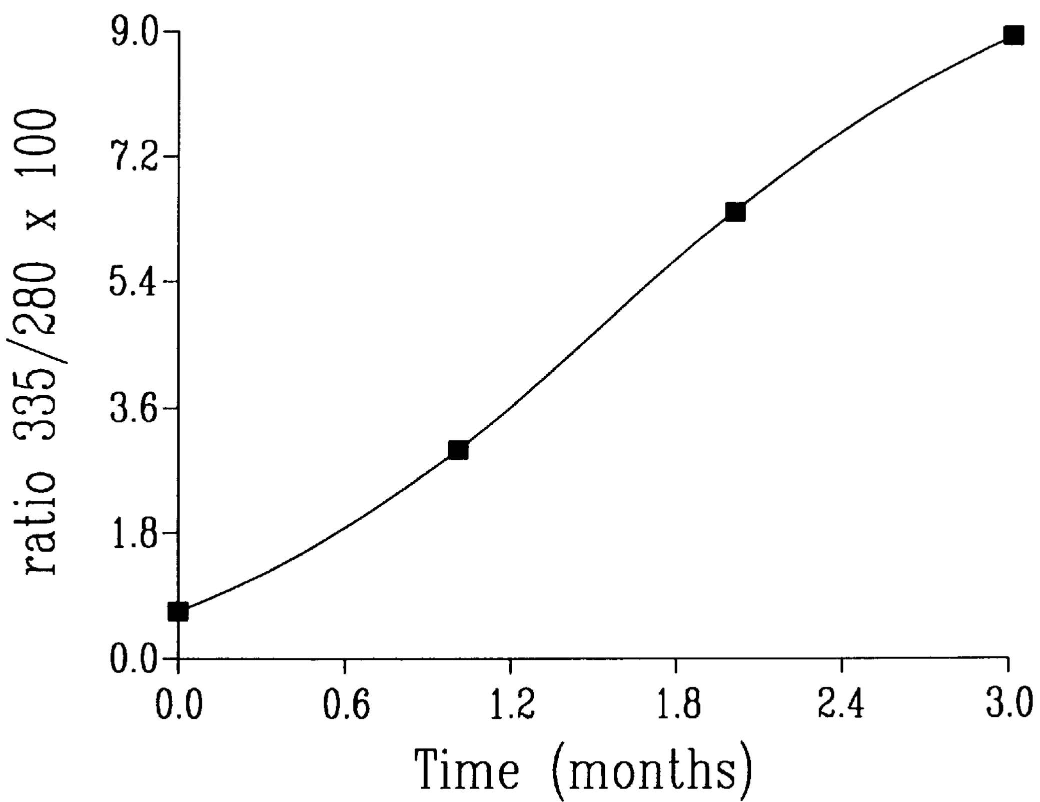
FIG. 1 is a curve of the detection of AGE modifications of a monoclonal IgG antibody in vitro over a three-month period, by measuring pentosidine residues (O.D.335) and correcting for amount of protein (O.D.280)

In diabetic and/or rheumatoid arthritis (RA) patients with elevated blood glucose levels and/or oxidative stress, a large number of proteins can be non-enzymatically glycated, whereby glucose binds to the exposed amino acids lysine and/or arginine. With time, the sugar is bound irreversibly. Proteins with this modification are said to have advanced glycation end products (AGE) such as CML, imidazolone and pentosidine. One of the proteins that can be modified is immunoglobulin (IgG, IgM or IgA).

In accordance with the present invention, we have identified AGE modified IgG in patients with RA and in diabetics. We have, in addition detected circulating IgM antibodies which specifically recognize the IgG when it is modified with AGE. RA patients with these "auto"antibodies have been found to have aggressive disease, with many having vasculitis. Recent cross sectional studies have shown that the anti-AGE autoantibodies correlate with disease severity ($p=0.04$) and swollen joints ($p=0.008$) (Lucey, manuscript in preparation). Additionally RA patients lacking anti-AGE antibodies have a significantly lower disability index ($p<0.05$) than those with anti-AGE antibodies (Cranney, manuscript in preparation). The "auto"antibodies appear to block the clearance of AGE modified proteins and contribute to their build up as anti-AGE positive RA patients have significantly higher IgG-AGE antibodies than do anti-AGE negative RA patients ($p<0.05$) (Newkirk, manuscript in preparation). These studies provide important information about the roles of both the AGE-IgG and anti-IgG-AGE antibodies in the disease pathogenesis. AGE deposits have been found to co-localize with IgM and IgG in the perineurium and blood vessels of an anti-AGE positive patient who has polymyalgia rheumatica (manuscript in preparation). Such information facilitates the diagnosis of severe RA disease and has an impact on disease management.

Patients and controls

Sera from RA patients as well as from other rheumatic diseases with vasculitis such as Henoch Schonlein Purpura, ANCA(+) vasculitis, Giant Cell Arteritis, Kawasaki disease have been drawn from clinics at the Montreal General Hospital (Dr. P. Fortin), the Montreal Children's Hospital (Dr. C. Duffy) and from a vasculitis serum bank (for the more rare diseases) (Dr. G. Hoffman, Cleveland Clinic Foundation, Prof. Gros, Lubeck). Controls include sera from patients with osteoarthritis (Dr. J. P. Pelletier, Notre Dame Hospital), sponduloarthropathies (Dr. R. Inman, Toronto Western Hospital), Alzheimer's disease and adult dimentia (Ms. Boyle, Maimonides, Montreal) as well as diabetics (type 1 and 2) (Dr. R. Gardiner, Montreal General Hospital). Information on a number of different clinical parameters, blood glucose levels, glycated hemaglobin (HbAlc) was drawn from the charts.

Rheumatoid factor assay

RF was detected by both nephelometry and by ELISA. IgG of all four subclasses (kindly provided by Prof. R. Jefferis) were used as target antigens to define the specificity. Monoclonal RF, BOR, KAS and RIV were used as standards, and were also modified by glycation in vitro (see below).

In vitro AGE modification of Ig and other proteins and measurement of protein-AGE Purified IgG of all four subclasses, IgM and IgA as well as other proteins of interest are sterilized by passing through a 20$\mu$ filter and then incubating in vitro with glucose (0.3 g/ml) for three months at 37° C., in order to generate the fully AGE-modified proteins. The amount of AGE modification on IgG was determined by measuring the optical density at 335 nM where the browning or pentosidine epitopes on the proteins can be detected (Pokharna et al., J. Ortho. Res., 13:13–21, 1995). By correcting for the amount of protein, as measured at O.D. 280, the AGE modifications which occur with time, on the purified IgG, IgA, IgM or other control proteins when incubated with sucrose at 37° C. can be followed.

Nitroblue tetrazolium (NBT) colorimetric method

For this assay, which has been modified from previously published methods (Mashiba et al., Clin. Chim. Acta, 212:3–15, 1992), serum was divided into an antibody/immune complex rich fraction and "other" proteins using a polyethylene glycol precipitation (PEG) method we have developed in the laboratory. For this 100 $\mu$l of serum is incubated with PEG 8000 to a final concentration of 2.5% and incubated for 30 minutes at 4° C. The samples are centrifuged at 15,000 for 5 minutes. The supernatant is collected ("other" proteins) and the pellet (IgG containing immune complexes) is resuspended in 100 $\mu$l of PBS. In 96 well plates, 50 $\mu$l of the supernatant and resuspended pellets are added to the wells in duplicate. Standard curves are established with BSA-AGE and IgG-AGE proteins in the range of 0–1.5 mg/ml for BSA and 0–4 mg/ml for IgG-AGE. 100 $\mu$l of the NBT reagent (250 $\mu$M NBT in 0.1 M carbonate buffer, pH 10.35) is added to each well and the plate is incubated at 37° C. for 2 hours. The plate is read in an ELISA plate reader at OD 550. The amount of the AGE modified proteins in the fractions can be calculated using the IgG-AGE (for the pellet) and BSA-AGE (for the supernatant) standard curves.

Immunoblots for AGE-IgG detection

Validation of the NBT assay, and further structural characterization of the AGE epitope on IgG was done by immunoblotting. In brief, 1 $\mu$l of the immune complex fraction (as above) was resolved on 10% SDS polyacrylamide gels, under reducing conditions. After transfer to nylon membranes, the membranes were blocked with 0.1% TWEEN™ 20 in PBS for one hour at room temperature. The AGE determinant was detected using a two hour incubation at 37° C. with the monoclonal antibody 6D12™ (Wako) specific for CML (Mizutari et al., J Invest Dermatol 108:797–802,1997) diluted 1:1000 in PBS/TWEEN™. After washing the blots, the bound 6D12 was detected after incubating for 1 hour at 37° C. with HRP-anti-mouse IgG (1:30,000). A chemiluminescent substrate ECL (Amersham) was used, with visualization on BIOMAX™ film (Kodak). To identify the components in the immune complexes, the blots were stripped according to the ECL recommendations, and reprobed with HRP-anti-human IgG, IgM or C3 (diluted 1:30,000, Jackson, EY Labs), followed by visualization by chemiluminescence.

The relationship between the amount of circulating IgG-AGE and the presence of IgM anti-IgG-AGE antibodies was studied by comparing the immunoblots of 5 randomly selected RA patients with IgM anti-IgG-AGE with those of 5 RA patients, 8 diabetics, and 5 healthy individuals without IgM-anti-IgG-AGE. Following isolation of immune complexes (as described above), 15 $\mu$g of total protein were resolved in 10% SDS PAGE under reducing conditions and transferred as above for immunoblotting. The relative amounts of CML as detected by the monoclonal antibody 6D12 on the heavy and light chains of the IgG were determined by laser densitometry, and then corrected for the amount of total IgG (blots were stripped and reprobed with anti-human IgG).

Measurement of antibodies to immunoglobulin-AGE

Anti-Ig-AGE antibodies (of all three classes) were detected in serum or plasma, using an ELISA assay which we have established in the laboratory. For this AGE-modified IgG (all four subclasses), IgA or IgM (2 μg/ml) is used to coat the wells of an EIA plate (ICN). After washing the plates, the sera or plasma, diluted 1:1000 or greater in duplicate, were incubated with the AGE-modified Ig for 2 hours at 37° C. After washing the plates in PBS/TWEEN™ (0.1%), the bound antibodies were detected with peroxidase conjugated F(ab')2 fragments of anti-human IgM, IgA or IgG (Jackson) as appropriate. It is not technically possible to detect IgG anti-IgG-AGE antibodies. Thus, in order to detect the IgG response IgA-AGE and IgM-AGE are used to coat the plates. When an individual is found to have IgM anti-IgG-AGE antibodies, reactivity to all of the other classes of antibodies and the IgG and IgA responses are determined. The titers of the anti-Ig -AGE of all classes will be determined, by serial dilution.

The anti-AGE response when the AGE is on other proteins was also examined. For this, albumin-AGE, and aldolase-AGE collagen-AGE and keyhole limpet hemocyanin (KLH) (modified in vitro) are used.

In vitro glycation of IgG or IgM

Figure 2:
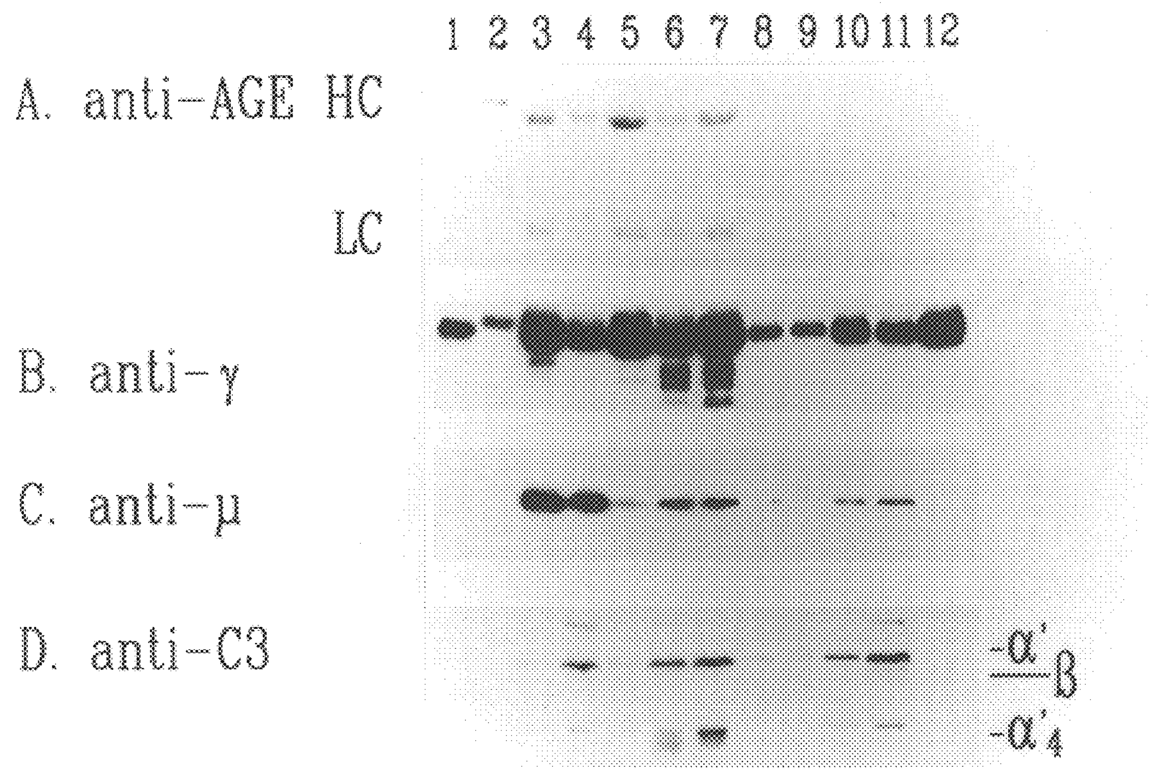
FIG. 2 illustrates a Western blot of purified IgG or 2.5% PEG precipitate (1 $\mu$l/lane) of sera, probed in panel A with monoclonal anti-$N^{\epsilon}$(carboxymethyl)lysine (CML) antibody (6D12) an AGE modified, panel B with anti-human Ig$\gamma$, in panel C with anti-human Ig$\mu$, and in panel D with anti-human C3.

In vitro, IgG is slowly modified, with almost complete modification after 3 months of incubation with glucose at 37° C. (FIG. 1). There is an accompanying increase in molecular weight (FIG. 2, Panel 1, lane 2). We have observed that even at –20° C., the AGE continues to be accumulated on IgG when stored as serum or in tissue culture media, but at a slower rate than at 37° C. This may account, in part for the limited "shelf-life" of antibodies. Measuring the change in the amount of pentosidine residues is useful for highly purified target proteins which are to be modified in vitro as the amounts used to follow the changes are small. Unfortunately it can not be used to follow the changes in the serum of patients with high blood glucose, as many proteins are modified by AGE. This necessitates a purification step.

We investigated the impact of glycation on RF activity and found that such activity is substantially reduced (BOR) or lost (RIV) when the IgM RF itself is glycated (Table 1).

During this investigation, we detected antibodies to the AGE-modified IgG in a patient with RA who had a particularly severe disease course.

Blood glucose levels and oxidative stress in rheumatoid arthritis

A subset of patients with RA have elevated blood glucose levels, often as a result of steroid treatment. Of 169 patients with RA, examined at the MGH, 18 had blood glucose levels greater than 6.5 mM/L (upper limit of normal), and 48 had glucose levels >5.5 mM/L. The elevations are modest, and of these, two were classified as diabetics. When followed over time, many of the RA patients maintain the "high" blood glucose profile for many years. One previous study has linked the presence of pentosidine modified proteins, the precise nature of which were unidentified, to disease activity in RA. In their study oxidative stress was implicated in this AGE modification (Takahashi et al. Br J Rheum 36:637–642, 1997).

Serum IgG-AGE levels in rheumatoid arthritis, diabetes and other disease groups

The frequency of detection of AGE modified IgG in immune complexes isolated from patients with a number of diseases is shown in Table 2.

TABLE 2

Number of patients positive for AGE modified proteins in immune complexes (2.5% PEG precipitate) or other serum proteins (2.5% PEG supernatant), by the modified nitroblue tetrazolium colorimetric assay

| Patient Group | Number | Immune complex | "other proteins" |
|---|---|---|---|
| RA | | | |
| (A) anti-AGE+ | 12 | 4 (33%) | 6 (50%) |
| (A) anti-AGE− | 11 | 1 | 0 |
| (B) anti-AGE+ | 4 | 0 | 1 |
| All RA | 27 | 5 (19%) | 7 (26%) |
| OA | 24 | 8 (33%) | 3 (13%) |
| AS + SpA | 15 | 1 | 0 |
| SS | 9 | 0 | 0 |
| Diabetics[1] | 9 | 2[2] (22%) | 4[3] (44%) |
| SLE 10 | 2 | 1 | |

RA (A) plasma stored for 2–3 years, normal controls used to establish cut off, stored 2–3 years;
RA (B) "new" prospective sera, using "new" normal controls for cut off.
OA and diabetics were "new" sera;
SLE and SS were stored plasma (stored 2–3 years);
[1]2 Type I, 7 Type II diabetics,
[2]correlation with HbAlc, r = 0.6, N.S.;
[3]correlation with HbAlc r = 0.8, p = 0.01.

Although the numbers are small, 20–33% of patients with RA, diabetes, SLE or osteoarthritis had elevated levels of

TABLE 1

| Subclass ± AGE | Binding (O.D.) of IgM monoclonal RFs to IgG subclasses with and without AGE modification | | | | | | | | |
|---|---|---|---|---|---|---|---|---|---|
| | BOR | BOR[1] | KAS | RIV | RIV[1] | BON[2] | LEA[2] | SOU[2] | BLA[2] |
| IgG1 | 2.8 | 1.4 | 0.969 | 2.124 | 0.009 | 0.137 | 0.058 | 1.256 | 0.220 |
| IgG1-AGE | 0 | | 0 | 0 | | 0.062 | 0.032 | 0.033 | 0.052 |
| IgG2 | 0.599 | | 2.342 | 1.550 | | 1.668 | >3.0 | 1.137 | >3.0 |
| IgG2-AGE | 0 | | 0 | 0 | | 0.109 | 0.126 | 0.067 | 0.069 |
| IgG3 | 0.005 | | 2.9 | 0.022 | | 0.225 | 0.093 | 0.164 | 0.176 |
| IgG3-AGE | 0 | | 0 | 0 | | 0.087 | 0.054 | 0.036 | 0.041 |
| IgG4 | 0.338 | | 1.445 | 0.671 | | 0.581 | 0.469 | 0.747 | 3.0 |
| IgG4-AGE | 0 | | 0 | 0 | | 0.077 | 0.037 | 0.055 | 0.048 |
| Fc | 1.001 | 0.381 | | 0.523 | 0.0 | | | | |

[1]In vitro AGE modified RF;
[2]Sera from patients with mixed essential cryoglobulinemia (kindly provided by Dr. V. Agnello, Boston, BOR, KAS and RIV were purified IgM RFs.

Figure 3:
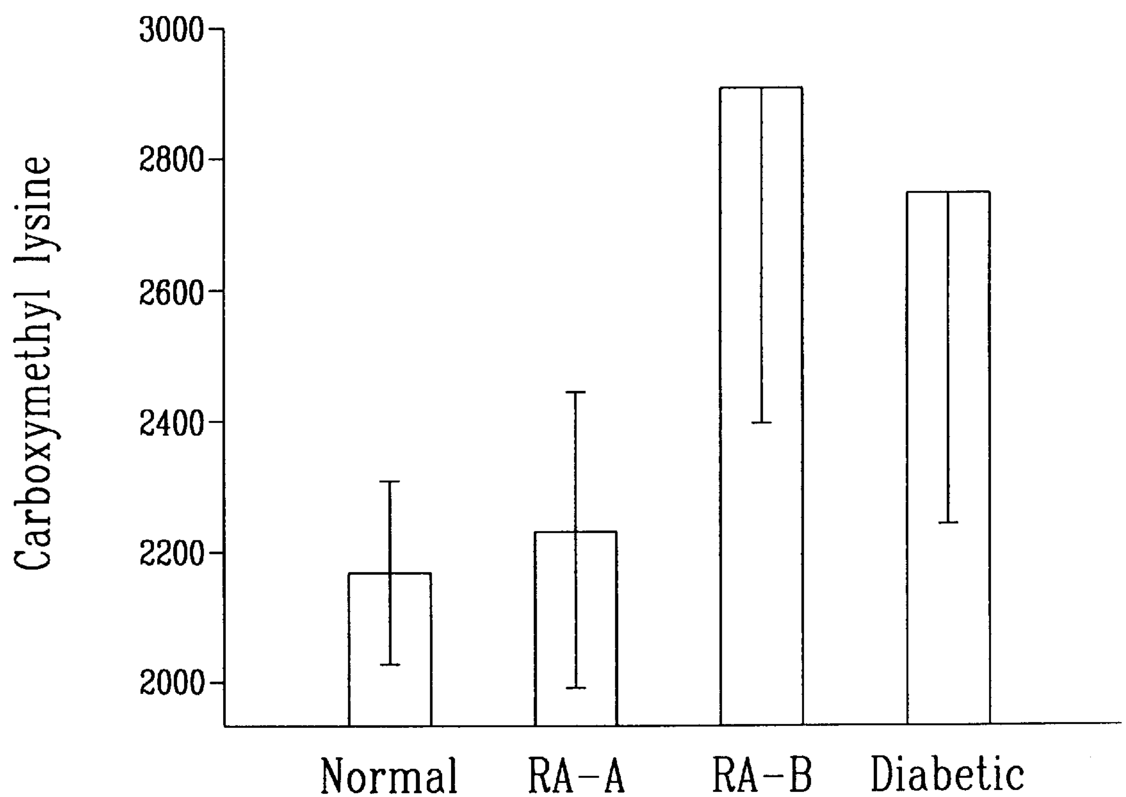
FIG. 3 illustrates a graph of the relative amounts of $N^{\epsilon}$(carboxymethyl)lysine (CML) as detected in immunoblots of the heavy chain of IgG from immune complexes, when corrected for total IgG, isolated from 5 normal individuals; 5 patients with RA who lacked circulating anti-IgG- AGE antibodies (RA-A); 5 RA patients with circulating anti-IgG-AGE antibodies (RA-B); 8 diabetics (3 with type 1 diabetes mellitus without anti-IgG-AGE antibodies, 2 with type 1 diabetes with anti-IgG-AGE antibodies, and 3 with type 2 diabetes). The mean and 95% confidence intervals are plotted.

IgG-AGE, compared to 7% of patients with ankylosing spondulitis, and other sponduIo arthropathies, with no patient with Sjögren's syndrome having elevated IgG-AGE. Normal controls were used to designate the cut off values. When the amount of AGE-IgG was calculated [based on an IgG-AGE standard curve] the values ranged from 0–0.8 mg/ml, in the RA, diabetic and OA patients whereas the IgG-AGE in SLE patients ranged from 0–0.3 mg/ml. Interestingly, the diabetics, who were selected on the basis of their poor blood glucose control, were found to have the highest amount of AGE on "other" serum proteins, when compared to the other groups studied, and importantly, this correlated with the HbAlc levels (r=0.8, p=0.01), even in this group of nine. From our studies, using a monoclonal antibody 6D12™ specific for CML (Mizutari et al., J Invest Dermatol 108:797–802,1997), the AGE appears to be primarily on IgG, both heavy and light chain (FIG. 3) and not on IgM in the RA patients. This is not surprising given the much shorter half-life of IgM compared to IgG. In other studies we have detected CML and imidazolone on the heavy chains and light chains of IgG from diabetics (both type 1 and 2) as well as from patients with RA (Newkirk et al. Arthritis Rheum. 40(suppl 1):S247, 1997 and FIG. 3). Recently we have detected imidazolone (AGE modified arginine) co-localizing with IgG and IgM in the perineurium and blood vessels of a patient with polymyalgia rheumatica (data not shown, manuscript in preparation).

The autoantibody response in rheumatoid arthritis—Rheumatoid factors

We were interested in determining whether RFs could bind to AGE modified IgG. Using monoclonal RFs from patients with mixed cryoglobulinemia, we have demonstrated that when the lysines and arginines are modified by AGE, there is no detectable RF binding (Table 1). This implicates the lysine and arginine residues as being important since they are in, or adjacent to the protein A and putative RF contact point (region 249–255). Not only lysines in the Fc region, however, are AGE modified, since we have identified by immunoblot analysis, using the anti-AGE antibody 6D12™ (Mizutari et al., J Invest Dermatol 108:797–802,1997), the AGE epitope on light chains (FIG. 3 Panel 1, lanes 3–7) both of in vitro modified IgG and in the immune complex IgG from patients with RA.

Anti-Immunoglobulin-AGE antibodies

IgM anti-IgG-AGE antibodies were detected in 48% of RF positive patients with RA which represented 36% of 153 RA patients total (Table 3). High titer anti-AGE antibodies were found in the subset of patients with aggressive destructive arthritis. In three index patients the presence of the antibodies correlated with vasculitis. All three had elevated levels of IgG-AGE as measured by NBT and immunoblot (FIG. 2). All three of the patients were treated with corticosteroids which likely contributed to their observed elevated blood glucose.

TABLE 3

Number of Rheumatic Disease, and other patient groups positive for Anti-IgG-AGE or bovine serum albumin (BSA)-AGE antibodies in patients with groups

| Patient Group (# tested) | IgM Anti-AGE-IgG positive | IgM Anti-AGE-BSA positive | IgG Anti-AGE-BSA positive |
|---|---|---|---|
| Rheumatoid Arthritis | | | |
| RF positive (114) | 20 | 9/35 | 6/35 |
| RF negative (41) | 0 | 0 | |
| Osteoarthritis[1] (40) | 0 | NA | |
| Ankylosing spondylitis, plus spondyloarthropathies[2] (15) | 0 | NA | |
| SLE | | | |
| RF positive (12) | 4 | 0 | |
| RF negative (21) | 0 | 0 | |
| Mixed essential cryoglobulinemia | | | |
| RF positive (8) | 1 | | |
| RF negative (2) | 0 | | |
| Primary Sjögren's syndrome (10) | 2* | 0 | |
| Adult Still's disease (8) | 0 | NA | |
| Alzheimer's disease (10) | 0 | NA | |
| Adult dementia (10) | 0 | NA | |
| Normal controls (10) | 0 | | |
| Diabetics[3] (14) | 2** | 2 | |

*of 4 RF positive;
**RF+, both type 1;
[1]24 were kindly provided by Dr. J. P. Pelletier, Notre-Dame Hospital, Montreal;
[2]kindly provided by Dr. R. Inman, Toronto;
[3]7 Type 1, 7 Type 2 diabetics We also investigated the presence of these antibodies in a number of other diseases where blood glucose abnormalities occur and as can be seen from Table 3, only patients with RFs also were found to have the anti-AGE antibodies, suggesting the immune response was linked.

In one group of RA patients, the IgA-anti-IgG-AGE response was also measured and we observed that the titers and frequency was much lower than the IgM response. The IgA response may be important in diseases such as Henoch Schonlein Purpura, Crohn's and Coeliac disease where IgA RF have been identified.

We have investigated the specificity of the polyclonal RFs and the anti-IgG-AGE antibodies in patients with RA. As can be seen in Table 4, the binding specificity's of the RF are predominantly of the Wa classic pattern, namely to IgGl, 2 and 4 but not IgG3. In contrast the anti-AGE specific antibodies appear to recognize the IgG3-AGE molecule much better than the other subclasses. This reconfirms that these two populations of antibodies are indeed distinct and may be due to the modified lysines or arginines in the hinge region of IgG3.

TABLE 4

Specificity of polyclonal RFs and anti-IgG-AGE antibodies for IgG subclasses in patients with rheumatoid arthritis

| Specificity | IgM RFs | IgM anti-IgG-AGE |
|---|---|---|
| "Wa" IgG1,2,4 | 18/53 (34%) | 4/37 (10%) |
| IgG3 > IgG1,2,4 | 1/53 (2%) | 16/37 (43%) |

To further characterize the binding specificity's, we also examined the ability of the anti-IgG-AGE antibodies to bind AGE on other proteins such as albumin and muscle aldolase. The antibody recognition of the AGE epitope on these proteins is much lower than that to the IgG molecule itself.

Thus neighboring amino acids, around the AGE likely contribute to the epitope(s) recognized by the antibodies.

To date the elevated titers of anti-IgG-AGE appear to be relatively RA specific, although for some disease groups the numbers are small. It will be important, in particular, to test additional diabetics (both type I and II), as well as other disease groups that are known to have circulating RFs, such as Henoch Schonlein Purpura, Crohn's and Coeliac disease.

DISCUSSION

In accordance with the present invention, we show that in a milieu of high blood glucose and/or oxidative stress, IgG becomes non-enzymatically glycated. This glycation affects the function of the antibody both in terms of its recognition of antigen and in its affector functions, mediated through the Fc portion. B-cells that express antibodies specific for the Fc portion of IgG (namely RFs), could bind the IgG-AGE (especially if the modification was in the Fab portion), endocytose, and process the altered self. The AGE-peptide would then be presented to the T-cell by the B-cell MHC complex, and an immune response to the IgG-AGE could ensue. These anti-IgG-AGE antibodies, as we detect in a subset of RA patients would thus result. Depending on the amount of both the IgG-AGE and the anti-IgG-AGE present, the patients could develop an inflammatory response. IgG-AGE in the absence of the "auto"antibodies would not necessarily be pathogenic. Also, the presence of only the anti-IgG-AGE (the autoantibody) but not the IgG-AGE (the antigen) would not lead to an inflammatory response. The latter situation would occur when the blood glucose is kept normal and non-enzymatic glycation is prevented. We speculate that the antibodies directed to IgG-AGE may inhibit the clearance of AGE modified proteins through the RAGE (receptor for AGE) or scavenger receptors. By thus inhibiting the degradation, a build up of the AGE modified proteins could be anticipated which could contribute to both the vasculitis and amyloid deposits.

We have not, to date, detected IgM anti-IgG-AGE antibodies in any patient who is RF negative. This suggests that these immune responses are linked. We speculate that RF expressing B-cells likely endocytose and process the altered self, AGE-modified IgG and then present it to the T-cells. There is, however, no correlation between the RF titer and the anti-IgG-AGE titer in the cross-sectional RA population tested. The RA patients with the highest titers of anti-AGE antibodies (titers of 1:2,000 to 1:10,000), have very severe arthritis and in general have a vasculitis component. In addition, the specificity differences that we detect (RFs binding predominantly to IgG1, 2 and 4 but not 3 in contrast to the anti-AGE antibodies that preferentially recognize the IgG3 subclass) confirm that these are different populations of antibodies.

When patients are treated with corticosteroids, used to immunosuppress their disease, there is often an elevation of blood glucose. In the 1950's it was recognized that there appeared to be a steroid induced epidemic of RA vasculitis (Kemper et al. Ann. Intern. Med. 46:831–851, 1957). It is possible that because of the elevation of blood glucose caused by the steroid treatment, the IgG became glycated, thus providing a target for circulating anti-AGE antibodies. One of the RA patients studied, not only had vasculitis, but also had extensive amyloid deposits. We speculate that since AGE-modified proteins have been identified in amyloid deposits, perhaps the anti-IgG-AGE antibodies contribute to this process by inhibiting their removal through AGE-specific receptors.

The receptor for AGE is also implicated in brain lesions seen in Alzheimer's disease (Yan et al., Nature, 382:685, 1996). It was therefore of interest to note that no AD patient had circulating anti-AGE antibodies (Table 3). Several groups have observed that RA patients are apparently protected from AD (Yan et al., *Nature,* 382:685, 1996; Myllykangas-Luosujarvi et al., *Br. J. Rheumatol.,* 33(5):501–502, 1994), although the mechanism is currently unknown. We speculate that the anti-AGE antibodies may play a role in this protection.

These antibodies clearly have the potential to impact not only on the pathogenesis of RA, but possibly on several other diseases where blood glucose abnormalities and/or oxidative stress are observed. The detection and measurement of the anti-IgG-AGE antibodies and the AGE-modified IgG are important advances in the diagnosis of severe RA. Therapeutic practices such as the use of steroids in the treatment of this disease may require careful monitoring of this antigen/antibody system.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for the diagnosis of severe diseases in patients, which comprises the steps of:

a) incubating a solid support coated with an advanced glycation end products IgG (AGE-IgG) antibody with a biological sample from said patient for a time sufficient for an immunoreaction to occur; and b) determining the presence of AGE-IgG autoantibodies present in said sample; whereby the presence of AGE-IgG autoantibodies in said patient's sample is indicative of a severe disease.

2. The method of claim 1, wherein the severe disease diagnosed is selected from the group consisting of Rheumatoid arthritis, atherosclerosis, amyloidosis, diabetes, Henoch Schonlein Purpura, Crohn's disease and Coeliac disease.

* * * * *